United States Patent [19]
Ohman et al.

[11] Patent Number: 6,033,364
[45] Date of Patent: Mar. 7, 2000

[54] METHOD OF ASSESSING REPERFUSION AFTER THROMBOLYTIC THERAPY

[75] Inventors: E. Magnus Ohman, Durham, N.C.; Robert H. Christenson, Joppa, Md.; Robert M. Califf, Durham, N.C.; Mary Ann O'Hanesian, Durham, N.C.; Kristina N. Sigmon, Durham, N.C.

[73] Assignee: Duke University, Durham, N.C.

[21] Appl. No.: 08/966,848

[22] Filed: Nov. 7, 1997

Related U.S. Application Data

[63] Continuation of application No. 08/516,159, Aug. 17, 1995, abandoned.

[51] Int. Cl.$^7$ ............................................. A61B 5/60
[52] U.S. Cl. ........................... 600/300; 600/301; 128/898
[58] Field of Search ................................. 600/300, 301, 600/481, 483; 128/898

[56] References Cited

U.S. PATENT DOCUMENTS

| 5,246,001 | 9/1993 | Ohman et al. | 128/630 |
| 5,290,678 | 3/1994 | Jackowski | 422/56 |

OTHER PUBLICATIONS

R.H. Christenson et al; Combining Myoglobin and Clinical Variables for Assessing Coronary Reperfusion After Thrombolytic Therapy; *Journal of the American College of Cardiology* (Feb. 1995) Abstract 148A.

E.M. Ohman et al; Noninvasive detection of reperfusion after thrombolysis based on serum creatine kinase MB changes and clinical variables: *American Heart J*. 126, pp. 819–826 (1993).

P. Klootwijk et al; Noninvasive Assessment of Reperfusion and Reocclusion After Thrombolysis in Acute Myocardial Infarction; *Am. J. Cardiol* 72 pp. 75Q, 81–84Q (1993).

E.M. Ohman and R.H. Christenson; Noninvasive Assessment of Myocardial Reperfusion and REocclusion; *Current Review of Interventional Cardiology* 6, pp. 6.2–6.15 (E.J. Topol & P.W. Serruys, Eds., 1994).

T. Laperche et al; Patterns of Myoglobin and MM Creatin Kinase Isoforms Release Early After Intravenous Thrombolysis or Direct Percutaneous Transluminal Coronary Angioplasty for Acute Myocardial Infarction, and Implications for the Early Noninvasive Diagnosis of Reperfusion; *Am. J. Cardiol* 70 (1992) Abstract only.

J. Abe et al; Myocardial reperfusion can be predicted by myoglobin/creatinekinase ratio of a single blood sample obtained at the time of admission; *Am. Heart J*. 126 (1993) Abstract only.

J. Ishii et al; Early detection of successful coronary reperfusion based on serum myoglobin concentration: Comparison with serum creatine kinase isoenzyme MD activity *Am. Heart J*. 128 No. 4 (1994) Abstract only.

*Primary Examiner*—Robert L. Nasser
*Attorney, Agent, or Firm*—Myers Bigel Sibley & Sajovec

[57] ABSTRACT

The present invention is a method of diagnosing the presence of a persistent occlusion in a myocardial infarct patient undergoing thrombolytic therapy. The method comprises detecting a series of five variables from the patient and then generating the probability of the presence of a persistent occlusion from those variables. The first variable comprises a serum creatine kinase MB (CK-MB) level from a patient at the onset of thrombolytic therapy. The second variable comprises a second CK-MB level in the patient at a predetermined time after the onset of thrombolytic therapy. The third variable comprises the presence or absence of chest pain a predetermined time after the onset of thrombolytic therapy. The fourth variable comprises the serum myoglobin level in the patient at a predetermined time after the onset of thrombolytic therapy. In a preferred embodiment of the present invention, the second, third and fourth variables are detected within 30 minutes of each other and within about 1 to about 3 hours after the initial variable is detected. In an alternate embodiment a fifth variable reflecting the time from onset of chest pain to the beginning of thrombolytic therapy is included in the regression model.

13 Claims, 2 Drawing Sheets

CLINICAL IMPLICATIONS OF A COMBINED MODEL OF CK-MB SLOPE, MYGLOBIN AND CLINICAL VARIABLES FOR NONINVASIVE DETECTION OF REPERFUSION STATUS

PERSITENT OCCLUSION
(TIMI GRADE FLOW 0-1)

| PROBABILITY | SENSITIVITY | SPECIFICITY | CARDIAC CATH** | PATENCY WITH RESCUE PTCA* |
|---|---|---|---|---|
| 0.80 | 13% | 99% | 5% | 78% |
| 0.50 | 48% | 91% | 19% | 85% |
| 0.30 | 78% | 80% | 35% | 92% |
| 0.20 | 87% | 74% | 42% | 94% |
| 0.10 | 96% | 53% | 58% | 95% |

PATENCY (TIMI GRADE FLOW 2 AND 3)

\* PATENTCY WITH RESCUE PTCA REFLECTS TO TOTAL PATENCY ACHIEVED FROM BOTH RESCUE PTCA WHICH WAS APPLIED TO THE PATIENTS THAT WERE IDENTIFIED AS CLOSED BASED ON THE PREDICTIVE VALUE IN ADDITION TO THOSE FROM THROMBOLYSIS ALONE (75%). THESE VALUES ARE BASED ON AN 85% SUCCESS RATE WITH RESCUE PTCA.

\*\* CARDIAC CATH REFLECTS THE PROPORTION OF PATIENTS THAT WOULD HAVE BEEN CATHED BASED ON THE LEVEL OF PROBABILITY OF PERSISTENT OCCLUSION.

FIG. 2.

METHOD OF ASSESSING REPERFUSION AFTER THROMBOLYTIC THERAPY

This application is a continuation of application Ser. No. 08/516,159, filed Aug. 17, 1995, now abandoned.

FIELD OF THE INVENTION

The present invention relates to methods of determining if reperfusion has occurred after thrombolytic therapy during a myocardial infarction.

BACKGROUND OF THE INVENTION

Early and sustained coronary artery patency after thrombolytic therapy has been implicated as one of the most important predictors of short and long term survival after acute myocardial infarction. Between 20% and 40% of patients receiving thrombolytic therapy fail to recanalize the infarct-related artery during the first few hours. Rescue angioplasty and selective infusion of fibrinolytic agents have been used successfully to restore patency of the infarct-related artery. Patients with successful rescue angioplasty have been noted to have similar long-term survival as patients who reperfuse after thrombolytic therapy alone, suggesting that procedures aimed at restoring patency after thrombolytic therapy has failed are beneficial in selected patients.

Acute coronary arteriography has to date been the only reliable method to identify patients who have failed to reperfuse. In the Thrombolysis Angioplasty in Myocardial Infarction (TAMI) 5 study a strategy using acute angiography coupled with rescue angioplasty was noted to be associated with a better overall clinical outcome after thrombolysis. However, performing acute angiography on all patients with acute myocardial infarction after thrombolysis is costly and not possible in most U.S. hospitals or in the world.

The critical importance of patency of the infarct-related artery for in-hospital and long-term survival has been documented by several studies. To non-invasively identify the subset of patients who have failed to restore patency or have incomplete reperfusion after intravenous thrombolytic therapy could allow these patients to undergo rescue angioplasty or more aggressive pharmacologic approaches.

Previous studies have examined clinical markers of reperfusion. These have included the resolution of chest pain or reperfusion arrhythmias occurring after thrombolysis. Arrhythmias have not been useful in three studies as a reliable marker of reperfusion, with sensitivities ranging between 37% and 63%. Resolution of chest pain has been a better marker of reperfusion, but has clinical disadvantages as patients perception of chest pain during myocardial infarction can be hard to interpret. Nevertheless, patients who have complete resolution of chest pain during thrombolytic therapy have a highly significant association with patency of the infarct-related artery (p=0.0005) documented during acute angiography. However, resolution of chest pain after thrombolysis is insufficient as the sole marker of reperfusion as only a small proportion of patients exhibit this phenomena.

A variety of intracellular components in the myocardium have been used to assess reperfusion. These markers have included myoglobin, myosin light chains, troponin T and both the MM and MB isoenzyme of creatine kinase (CK). Newly isolated tissue isoforms of CK-MB also hold promise as reliable predictors of reperfusion, but are limited by relative long assay time and lack of availability in most chemistry laboratories. In general these studies have examined the time to peak on the CK-MB release curve or used methods that require prolonged assay times. Both of these factors do not allow for early and rapid triage of patients after thrombolysis to enhance the care of patients who have failed to restore patency.

SUMMARY OF THE INVENTION

The present invention is a method of diagnosing the presence of a persistent occlusion in a myocardial infarct patient undergoing thrombolytic therapy. The method comprises detecting a series of variables from the patient and then generating the probability of the presence of a persistent occlusion from those variables. The first variable comprises a serum creatine kinase MB (CK-MB) level from a patient at the onset of thrombolytic therapy. The second variable comprises a second CK-MB level in the patient at a predetermined time after the onset of thrombolytic therapy. The third variable comprises the presence or absence of chest pain a predetermined time after the onset of thrombolytic therapy. The fourth variable comprises a serum myoglobin level in the patient at a predetermined time after the onset of thrombolytic therapy.

In another aspect of the present invention, the method further comprises the step of determining a fifth variable comprising the time from onset of myocardial infarct symptoms in said patient to the administration of thrombolytic therapy to the patient and generating the probability of the presence of a persistent occlusion from the first through fifth variables.

In an additional aspect of the present invention, the second variable, the third variable and the fourth variable are detected within thirty minutes of one another, and the second variable, the third variable and the fourth variable are detected from 1 to 3 hours after the onset of thrombolytic therapy. In a further aspect of the present invention the second variable, the third variable and the fourth variable are detected concurrently one and one-half hours after the onset of thrombolytic therapy.

DESCRIPTION OF THE DRAWINGS

FIG. 2 presents data relating to the clinical implications of the inventive method in assessing reperfusion status in patients following thrombolytic therapy after acute myocardial infarction.

DETAILED DESCRIPTION OF THE PREFERRED EMBODIMENT

Figure 1:
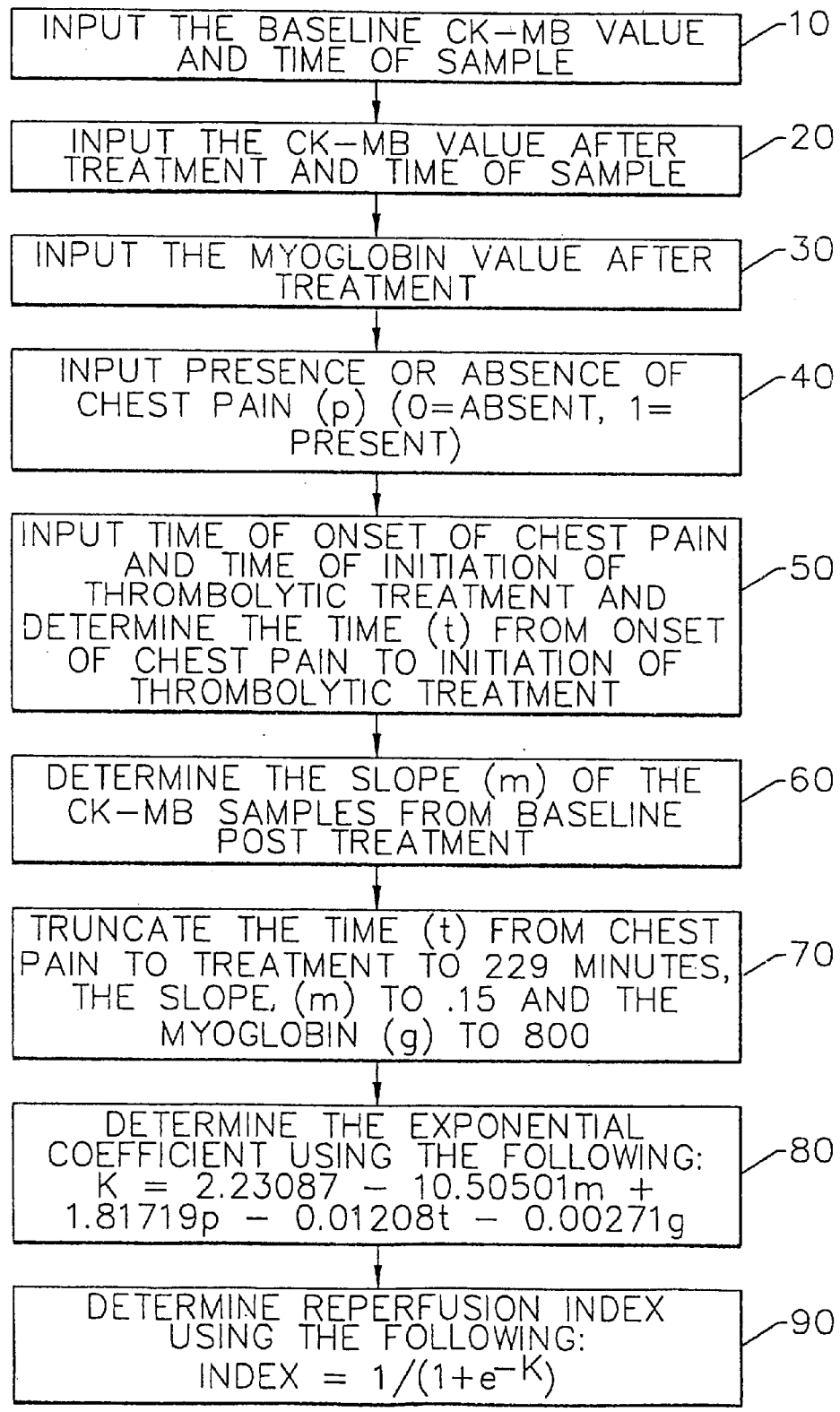
FIG. 1 is a flow diagram of the computer program which may be used to determine the reperfusion index of a patient.

The present invention is a method of determining if reperfusion occurs in a patient having a myocardial infarct and receiving thrombolytic therapy. The method of the present invention utilizes a combination of creatine kinase (CK-MB) measurements before and after thrombolytic therapy and serum myoglobin level after thrombolytic therapy in combination with clinical information to determine the reperfusion during myocardial infarction. Measuring changes in serum CK-MB levels in conjunction with two clinical variables and the patient serum myoglobin level after starting thrombolytic therapy, can be used to more accurately identify patients who had failed to restore patency. Using such an approach it has been possible to develop a more accurate computerized model for the early noninvasive detection of reperfusion status within the first three hours of starting thrombolytic therapy, allowing more accurate early triage of such patients for acute cardiac catheterization and consideration for rescue angioplasty.

The method of the present invention involves the use of five variables in determining whether persistent occlusions are present in a patient after thrombolytic therapy. Blood samples are taken before and after thrombolytic therapy and assayed for creatine kinase MB levels. The blood sample taken after thrombolytic therapy is also assayed for myoglobin level. Clinical variables of chest pain after therapy and the time from onset of chest pain to the beginning of thrombolytic therapy, the two CK-MB levels, and the myoglobin level are input values for a statistical model which results in the probability of the presence of a persistent occlusion.

Samples of blood are taken from the patient having already been diagnosed as having a myocardial infarction. These samples are taken prior to the beginning of thrombolytic therapy (e.g. administration of tissue plasminogen activators, streptokinase, urokinase or APSAC). The baseline sample is preferably taken within 6 hours of the onset of symptoms of the myocardial infarct (i.e. chest pain) and within 1 hour of the beginning of thrombolytic therapy. The time of sampling is recorded. The blood sample is then analyzed for serum creatine kinase MB (CK-MB) level.

After thrombolytic therapy has begun, a second blood sample is taken from the patient. This sample is take between about 1 and about 3 hours and most preferably about 90 minutes after commencing thrombolytic therapy and the taking of the baseline sample. This sample is assayed for CK-MB level and is also assayed for myoglobin level and the time of the sample is recorded.

Blood samples for the MB isoenzyme of creatine kinase (CK-MB) are collected from indwelling venous lines. A total of 10 ml of blood is drawn at the baseline (before thrombolytic therapy) and post-thrombolytic times. Blood samples are preferably collected in tubes containing no anticoagulant. In preparing the samples for test, serum is separated by centrifugation at 1000 g and aliquoted within 90 minutes of collection into screw-top freezer vials. Samples may be stored in −70° C. until analysis. Various methods of CK-MB analysis are known, however, samples have been analyzed by two methods for CK-MB determination; a commercially available immunochemical assay based on the method of Wicks et al., Clinical Chemistry, 1982, 28:54–58, and; by a rapid two-site immunoassay (ICON QSR CK-MB; Hybritech Inc., San Diego, Calif.) based on a dual monoclonal antibody technique, Piran et al., Clinical Chemistry, 1987, 33:1517–1520. The correlation between the two assays was excellent; r=0.99 (ICON=1.89×Roche+13 ng/ml; Sy/x=12.2 ng/ml). While both methods yield acceptable results, the commercially available mass assay (Hybritech ICON QSR) is preferred. Excellent correlation between the standard activity assay (Roche) and the mass assay exist, however, the latter allows for quick determination of serum CK-MB levels required for a diagnostic test being used during the early post thrombolysis phase, where minimizing delays are essential.

Although there are numerous methods available for myoglobin measurement in serum, the most reliable, quantitative, sensitive and specific tests are so called "immunoassays" based on antibody technology. Samples for inclusion in this noninvasive reperfusion assessment strategy were performed with a two-site immunoassay based on two murine monoclonal antibodies available commercially from Baxter Diagnostics, Miami, Fla. Technically, the first of these myoglobin antibodies is bound to a glass fiber matrix; when patient sample is added, this first antibody "captures" any myoglobin present in the specimen, immobilizing it to the glass fiber matrix. For detection and quantification of the immobilized myoglobin, a second anti-myoglobin antibody is added which reacts with the 1st antibody-myoglobin complex to form a [1ist antibodymyoglobin-2nd antibody] sandwich. The second antibody is conjugated to alkaline phosphatase, which allows myoglobin to be quantified by adding an alkaline phosphatase substrate and monitoring how much is converted to product. This myoglobin method demonstrates good agreement with other immunoassay methods (Alonsozana et al. Clin Chem 1994; 40:1123).

The single myoglobin measurement used in the model should be measured using the same specimen as was collected for the second CK-MB specimen. Therefore no additional blood or separate phlebotomy must be performed to obtain this additional information; this may be particularly important in patients receiving thrombolytic therapy.

As a clinical variable in the prediction of reperfusion, the presence or absence of chest pain in the patient after the commencement of thrombolytic therapy is assessed. This assessment may be carried out as a simple binary response (i.e. yes or no) as to the presence or absence of chest pain. A well recognized clinically used scale to determine the degree of severity of chest pain may be used that rates the degree of severity on a scale from 0 to 10 with 0 representing no chest pain, 2 representing mild chest pain, 5 representing moderate chest pain and 10 representing severe, extreme chest pain. The assessment of chest pain may be carried out any time after the commencement of thrombolytic therapy, preferably from 1 to 3 hours and most preferably 90 minutes after the therapy is begun. It is not essential that the assessment of chest pain and the second blood sample described above be taken concurrently. However, it is preferable that the second sample and the assessment occur within 30 minutes of each other and most preferably concurrently.

A second clinical variable which may be used in the prediction of reperfusion is the time from onset of chest pain to the administration of thrombolytic therapy. This time may be determined by calculating the difference between the time of onset of chest pain and the time thrombolytic therapy was first begun.

Through the combination of these five variables, a prediction of the reperfusion of a myocardial infarct can be made utilizing an empirically-based regression analysis model of the occurrence of persistent occlusions in myocardial infarct patients receiving thrombolytic therapy.

Using a rapid CK-MB assay and a myoglobin assay combined with clinical variables results in improved identification of patients who have failed to restore patency after thrombolysis. The assay used for CK-MB measurement is a commercially available assay (ICON QSR CK-MB, Hybritech Inc.) that takes 20 minutes to perform using a dual monoclonal technique. The assay for myoglobin was performed using the immunoassay available on the Stratus II analyzer (Baxter Diagnostics, Miami Fla.). The slope of CK-MB release is the variable most closely associated with reperfusion status. By inclusion of the selected clinical variables described above and the myoglobin level after thrombolytic therapy to the CK-MB model the capability of non-invasive detection of persistent occlusion after thrombolysis is further enhanced. The combination of these variables results in more accurate predictions than through the use of either CK-MB assays, myoglobin levels or clinical variables alone. The combination of these variables further provided increased accuracy over even the combination of CK-MB assays and clinical variables. This model can be applied during the early phase of infarction and give results within three hours of starting thrombolytic therapy. In a preferred embodiment, a computerized model is uploaded on a computer and can be placed in the clinical chemistry laboratory or emergency room to aid in the management of patients.

As seen in FIG. 1, the block diagram of the computer program of the computerized model illustrates the use of the method of the present invention.

Blocks 10, 20 and 30 represent the collection of data from the blood samples described above. As seen in block 10, the time and level of the CK-MB baseline sample is input and stored by the computer. This baseline sample represents the pre-therapy blood sample described above. Next, as seen in block 20, the time and level of CK-MB after therapy is input and stored. This second CK-MB level is taken between 1 and 3 hours after beginning thrombolytic therapy and corresponds to the second sample described above. Block 30 represents the myoglobin level after therapy.

Blocks 40 and 50 represent the input of clinical variables regarding the patient. As seen in block 40, the presence or absence of chest pain is input. In an alternate embodiment, the degree of chest pain could be input in place of the presence or absence of chest pain. Block 50 shows the input of the second clinical variable. From the time of onset of chest pain and the time at which thrombolytic therapy began, the time from onset of chest pain to the initiation of thrombolytic therapy is determined. The time (in minutes) from onset of chest pain to the initiation of therapy (t) is determined using the following equation:

$$t = t_4 - t_3$$

where $t_3$ is the time of onset of chest pain, and $t_4$ is the time of initiation of thrombolytic therapy. These values are input and stored for use in the predictive model as described below.

Blocks 60, 70, 80, and 90 represent the predictive determination of the persistence of the occlusion of the myocardial infarct patient. As seen in block 60, the slope of the line defined by the baseline and the post-therapy CK-MB assays is determined. The slope is calculated from the CK-MB assays using the following equation:

$$m = \frac{(L_1 - L_2)}{(t_1 - t_2)}$$

where $L_1$ = CK-MB baseline level
$L_2$ = CK-MB post-therapy level
$t_1$ = time of baseline sample
$t_2$ = time of post-therapy sample In block 70 truncation of the slope (m), the time from onset of chest pain to the beginning of therapy (t) and the myoglobin level (g) are truncated to simplify the mathematical computations. The slope (m) is truncated to 0.15 if the value of m is greater than 0.15. The time (t) is truncated to 229 minutes if the value of t is greater than 229 minutes. The myoglobin level (g) is truncated to 800.

Block 80 illustrates the calculation of the exponential coefficient of the model of reperfusion. The following linear combination of weighted variables is used:

$$K = C + A_1 m + A_2 p + A_3 t + A_4 g$$

where C is a constant (C=2.23087), m is the CK-MB slope, p is the chest pain clinical variable, t is the time from onset of chest pain to beginning of therapy, g is the myoglobin level and A1 through $A_4$ are the following weights:

$A_1$ = −10.5051;
$A_2$ = 1.81719;
$A_3$ = −0.01208;
$A_4$ = −0.00271

Preferably each of the above variables and weights are used in determining the exponential coefficient K, however, an alternate embodiment of the present invention uses only CK-MB slope and clinical chest pain information in prediction reperfusion. The weight $A_2$ reflects the weighting of the chest pain variable p for a binary presence or absence of chest pain. As will be understood by one of skill in the art, the value of $A_2$ may be modified using the methods described below to reflect the use of a scaled input for degree of chest pain. Utilizing the standard statistical analysis of the empirical database described below, a new weight may be obtained.

Having determined the exponential coefficient, block 90 illustrates the determination of the reperfusion index which is the probability of reperfusion. The reperfusion index is calculated using the following equation:

$$\text{index} = (1 + e^{-k})^{-1}$$

where K is the exponential coefficient described above. This combined regression model of CK-MB slope, myoglobin level and clinical variables generates the reperfusion index or probabilities of detection of a persistent occluded infarct-related artery or incomplete reperfusion after thrombolysis. Rather than describing a predefined cut-off value to be used by physicians for an individual patient, this model could be used with different levels of "aggressive" care. The implications of such an approach are shown in Table 1. Using this approach a decision to perform acute angiography with possible rescue angioplasty could be based on the combination of clinical data and changes in serum CK-MB, giving a probability of finding an occluded infarct-related artery or suboptimal reperfusion if the patient had acute cardiac catheterization. For example, in a young patient where long term survival may be critical, a low probability (0.1) could be used to decide a triage to acute cardiac catheterization. This would lead to the majority (58%) of such patients having angiography and only a small proportion (4%) of patients with closed infarct-related artery would be missed. For an elderly patient, a different level of probability may be used to assess reperfusion status. In such a patient, one may chose a probability of 0.3 to intervene. In this scenario, 78% of patients who failed to reperfuse would be identified, while only 35% of all treated patients would undergo cardiac catheterization. This approach could potentially lead to a 17% higher early patency rate compared with a conservative approach. As described below and for uniformity, the determination of whether reperfusion has occurred is based on the grade of flow following thrombolytic therapy. The flow of the infarct-related artery was graded according to the Thrombolysis in Myocardial Infarction (TIMI) Classification. The TIMI Study Group, New England Journal of Medicine, 1985, 312:932–936.

Recent studies have suggested that the attainment of TAMI grade 2 flow after thrombolysis may be insufficient in order to obtain myocardial salvage after thrombolytic therapy. The rapid assessment of changes in CK-MB levels after thrombolytic therapy has similar diagnostic yield when patients with TIMI grade 0 to 2 3flow are compared with patients with complete reperfusion (TIMI grade 3 flow). Thus, the above regression model can be used in the method of the present invention so that the majority (85%) of patients who had not had complete reperfusion can be identified.

The weighting factors of the above equations were determined using statistical analysis of an empirical database of actual patient experience. These values may be obtained through the use of readily available statistical analysis packages for personal computers such as those offered by SAS Institute of Cary, N.C. Other means of regression analysis will be apparent to one of skill in the art. See generally Snedecor et al., Statistical Methods, Seventh Edition, The Iowa State University Press, 1980. Changes in CK-MB levels between post-therapy samples and baseline samples were examined by the difference (Delta; Pre-IRA value minus baseline value), the slope (Delta divided by the time between the samples), and the ratio (Pre-IRA value divided by baseline value). Statistical comparisons of clinical variables and CK-MB changes and the patency status (outcome) were performed using logistic regression. Spline transformations were used and proper levels of truncation were developed. See Lee et al., American Journal of Medicine, 1986, 80:553–560. The following strategy was used to find clinical variables that might be used to augment the enzymatic prediction of patency status. Multiple linear regression was used to evaluate the relationship of clinical variables to perfusion status at acute angiography. The candidate variables included gender, age, race, weight, time to thrombolytic therapy after onset of symptoms, infarct location, and chest pain (scale 0–10) prior to acute angiography. By comparing the two models a final decision about clinically and statistically meaningful variables was then made. The best clinical variables and the optimal change in serum CK-MB and myoglobin level were then combined to yield an overall model. This final combined model was used to generate actual probabilities based on the data entered into the combined serum CK-MB, myoglobin and clinical model. Various strategies for using the myoglobin levels were also tested and a post-treatment level truncated at 800 is used in further analysis.

The above statistical analysis can be repeated incorporating additional data from current patient information into the empirical database. The empirically-based regression analysis described above may be augmented by additional empirical data from the current patient. By including the current patient in the empirical database, the weighting factors may be updated to reflect the additional data in the computerized regression model.

The foregoing is illustrative of the present invention, and are not to be construed as limiting thereof. The invention is defined by the following claims, with equivalents of the claims to be included therein.

That which is claimed is:

1. A method of determining if reperfusion has occurred in a myocardial infarct patient after receiving thrombolytic therapy, comprising:

(a) detecting a first variable comprising a first serum creatine kinase MB level in a myocardial infarct patient undergoing thrombolytic therapy at the an onset of said thrombolytic therapy; then (b) detecting a second variable comprising a second creatine kinase MB level in said patient a predetermined time after the onset of said thrombolytic therapy; and (c) detecting a third variable comprising a presence or absence of chest pain a predetermined time after the onset of said thrombolytic therapy;

(d) detecting a fourth variable comprising a serum myoglobin level in said patient a predetermined time after the onset of said thrombolytic therapy;

(e) generating a probability of the presence of a persistent occlusion from said first through fourth variables, the absence of a persistent occlusion indicating that reperfusion has occurred in said patient.

2. A method according to claim 1, wherein said second variable, said third variable and said fourth variable are detected within thirty minutes of one another, and wherein said second variable, said third variable and said fourth variable are detected from 1 to 3 hours after the onset of thrombolytic therapy.

3. A method according to claim 1, wherein said second variable, said third variable and said fourth variable are detected concurrently one and one-half hours after the onset of thrombolytic therapy.

4. A method according to claim 1, further comprising the step of:

determining a fifth variable comprising a time from onset of myocardial infarct symptoms in said patient to an administration of the thrombolytic therapy to said patient, and wherein said generating step comprises generating the probability of the presence of a persistent occlusion from said first through fifth variables.

5. A method according to claim 1, wherein said generating step is carried out with an empirically-based model of actual clinical experience.

6. A method according to claim 5, further comprising the step of updating said empirically-based model to include the clinical experience of said myocardial infarct patient.

7. A method according to claim 1, wherein said generating step is carried out with a regression model.

8. A method according to claim 1, wherein said first variable is detected within about 6 hours from an onset of symptoms in the patient and within about 1 hour of the onset of thrombolytic therapy.

9. A method of determining if reperfusion has occurred in a myocardial infarct patient after receiving thrombolytic therapy, comprising:

(a) detecting a first variable comprising a first serum creatine kinase MB level in a myocardial infarct patient undergoing thrombolytic therapy at an onset of said thrombolytic therapy; then (b) detecting a second variable comprising a second creatine kinase MB level in said patient a predetermined time after the onset of said thrombolytic therapy; and (c) detecting a third variable comprising a presence or absence of chest pain a predetermined the after the onset of said thrombolytic therapy;

(d) detecting a fourth variable comprising a serum myoglobin level in said patient a predetermined time after the onset of said thrombolytic therapy;

(e) detecting a fifth variable comprising a time from onset of myocardial infarct symptoms in said patient to an administration of the thrombolytic therapy to said patient;

(f) generating a probability of the presence of a persistent occlusion from said first through fifth variables, the absence of a persistent occlusion indicating that reperfusion has occurred in said patient;

wherein said first variable is detected within about 6 hours from an onset of symptoms in the patient and within about 1 hour of the onset of thrombolytic therapy;

wherein said second variable, said third variable and said fourth variable are detected within thirty minutes of one another;

and wherein said second variable, said third variable and said fourth variable are detected from 1 to 3 hours after the onset of thrombolytic therapy.

10. A method according to claim 9, wherein said second variable, said third variable and said fourth variable are detected concurrently one and on-half hours after the onset of thrombolytic therapy.

11. A method according to claim 9, wherein said generating step is carried out with an empirically-based model of actual clinical experience.

12. A method according to claim 11, further comprising the step of updating said empirically-based model to include the clinical experience of said myocardial infarct patient.

13. A method according to claim 9, wherein said generating step is carried out with a regression model.

* * * * *